United States Patent [19]

Lowndes et al.

[11] Patent Number: 5,994,395
[45] Date of Patent: Nov. 30, 1999

[54] COMPOSITION FOR CONTROLLING PARASITES

[75] Inventors: Philip Anthony Lowndes, Cambridge, United Kingdom; Stefan Kemmethmüller, Freiburg, Germany; Steven Craig Parks, Greensboro; Douglas Irvin Hepler, McLeansville, both of N.C.

[73] Assignee: Novartis Animal Health US, Inc., Greensboro, N.C.

[21] Appl. No.: 08/894,579

[22] PCT Filed: Feb. 15, 1996

[86] PCT No.: PCT/EP96/00658

§ 371 Date: Jan. 23, 1998

§ 102(e) Date: Jan. 23, 1998

[87] PCT Pub. No.: WO96/25852

PCT Pub. Date: Aug. 29, 1996

[30] Foreign Application Priority Data

Feb. 24, 1995 [CH] Switzerland ................. 541/95

[51] Int. Cl.[6] .................................................. A01N 43/16
[52] U.S. Cl. ............................................................ 514/460
[58] Field of Search .................................. 514/819, 460

[56] References Cited

U.S. PATENT DOCUMENTS

| | | | |
|---|---|---|---|
| 3,950,362 | 4/1976 | Aoki et al. | 260/343.2 R |
| 4,199,569 | 4/1980 | Chabala et al. | 424/180 |
| 4,310,519 | 1/1982 | Albers-Schonberg et al. | 424/181 |
| 4,346,171 | 8/1982 | Takiguchi et al. | 435/119 |
| 4,547,520 | 10/1985 | Ide et al. | 514/450 |
| 4,677,127 | 6/1987 | Böger | 514/346 |
| 4,696,945 | 9/1987 | Frei et al. | 514/450 |
| 4,959,386 | 9/1990 | Frei et al. | 514/450 |
| 4,988,824 | 1/1991 | Maulding et al. | 549/264 |

FOREIGN PATENT DOCUMENTS

| | | |
|---|---|---|
| 0 242 502 | 10/1997 | European Pat. Off. . |
| 2 220 856 | 1/1990 | United Kingdom . |
| 86/03941 | 7/1986 | WIPO . |
| 95/33380 | 12/1995 | WIPO . |

OTHER PUBLICATIONS

Bull. Soc. France Parasit, 8, 1990.
Interceptor, Flavour Tabs, Aug. 1994.
Lowndes, Program Product Profile, Feb. 4, 1992.
Merck Index, p. 128, 753, 887.

*Primary Examiner*—S. Mark Clardy
*Assistant Examiner*—Alton Pryor
*Attorney, Agent, or Firm*—Norbert Gruenfeld; Michael P. Morris; William A. Teoli, Jr.

[57] ABSTRACT

The present invention relates to a composition for controlling parasites, in and on animals, which comprises, as active ingredient, a combination, in variable proportions, of at least one parasiticidally active compound, in free form or in salt form, selected from the N-phenyl-N'-benzoyl-urea class of substances, and at least one parasiticidally active compound, in free form or in salt form, selected from the milbemycin, avermectin, milbemycin oxime, moxidectin, ivermectin, abamectin and doramectin classes of substances; to a method of controlling these parasites; to a process for the preparation of this composition; and to the use of this composition.

11 Claims, No Drawings

COMPOSITION FOR CONTROLLING PARASITES

This Application is a 371 of PCT/EP96/00658 filed Feb. 15, 1996.

The present invention relates to a composition that comprises a combination of at least two parasiticidally active substances and that is suitable for controlling pests in and on animals, to a method of controlling these parasites, to a process for the preparation of this composition, and to the use of this composition.

As is known, the life cycles of many parasites, in and on animals, are very complicated, which makes the control of these parasites, which without their effective control often cause considerable, for example economic, damage, extraordinarily difficult. Within the scope of the present invention, parasites are to be understood as comprising ectoparasites as well as endoparasites.

Ticks, for example, which are representatives of the ectoparasites, may feed exclusively on one host animal or also on several hosts. They settle on the host animal and feed on its blood. The females, fully replete with blood, drop off the host animal and then lay a large number of eggs in a suitable niche in the vicinity. The developing larvae then seek a new host animal in order to develop via the nymph stage into adults and once again become fully replete with blood. Certain species may migrate from one host animal to a second and even a third host animal. Ticks that are of economic significance from the aetiological standpoint belong mainly to the genera Amblyomma, Boophilus, Hyalomma, Ixodes, Rhipicephalus or Dermacentor, especially involved are the species *Boophilus microplus* and *B. annulatus*, most especially *B. microplus*. They are also responsible for the transmission of numerous diseases that may affect humans and animals. Bacterial, protozoan, rickettsial and viral diseases, in particular, are transmitted. The causative organisms of such diseases are transmitted especially by ticks that feed on more than one host. These diseases may lead to the weakening or even the death of the host animals. They usually cause high economic losses, for example as a result of the meat of productive livestock losing value, the usable skin being damaged, or the milk production being reduced Ticks are normally controlled by treating the affected animals with an acaricidally active composition in response to an actual infestation, that is to say curatively. The occurrence of ticks, for example on pasture ground, is greatly dependent upon seasonal weather conditions, and the ultimate infestation of the host animals depends, in addition, upon their resistance to the ticks. This means that a preventive control of the ticks is difficult and time-consuming since inter alia the risk of infestation by the pests and the animals' power of resistance to them can be estimated only with difficulty. In addition, when attempting a preventive control of the parasites, the potential infestation has to be monitored over a relatively long period, which causes additional problems. The reason why, nevertheless, a preventive control of the pests would be desired, is the fact, that relatively great damage has often already occurred by the time the curative control begins to act.

Fleas, another example of representatives of the ectoparasites, also have a very complex life cycle. For example, adult cat fleas (*Ctenocephalides felis*) and dog fleas (*C. canis*) normally live in the coat of the host cat and host dog. They feed on the blood of the host animal and lay their eggs in its coat. Since those eggs are not self-clinging, however, they generally soon fall off and can be found on the floor, on the carpet, in the dog basket or cat basket, on a chair used by the animal, in the garden and at all the other places with which the infested animal comes into contact. This means that the entire area where the animal lives is contaminated with flea eggs from which, within two days, the larvae develop. In the case of the larvae, a distinction is made between three stages of development, each of which lasts three days. In the last stage, the larvae spin their cocoons and change into pupae from which the young, mature fleas develop. The young adult fleas remain there until they sense the presence of an acceptable host animal, then they emerge from their cocoons and attempt to jump onto the host animal. It takes about three weeks, therefore, before an adult young flea capable of re-infesting the host animal develops from an egg. The young flea may, however, remain in its cocoon for months, possibly up to a year. On the other hand, under less than optimum conditions, the development from the egg to the adult young flea may take 4 to 5 months. Fleas require blood as food to reach their sexual maturity in order to reproduce. Flea larvae feed mainly on the excreta of the adult fleas that live on the host animal. Those excreta contain high proportions of undigested blood. The flea infestation of an animal, especially of a dog or a cat, has unpleasant accompaniments not only for the animal, but also for the keeper of the animal Such unpleasant effects lead, as far as the animal is concerned, for example, to local irritation, to annoying itchiness or even to allergies and often cause intense scratching. Furthermore, an animal infested with fleas is constantly exposed to the risk of being infected with representatives of Dipylidium spp., i.e. with tape worms, which are transmitted by fleas. In addition, fleas and their excreta may also lead to allergy-like skin disorders of many people, which in many cases forces them to give up keeping the animal. The effective control of fleas on animals, especially on productive livestock and pets, especially on dogs and cats, has therefore been desirable since time immemorial. The above-described long life cycle, a large proportion of which takes place away from the host animal, has a significant effect on the successful control of fleas on the host animal. Only when the described cycle can be broken, that is to say when the numerous flea eggs and flea larvae present in the environment of the host animal can be destroyed, the animal is protected from continual re-infestation by adult parasites. However, none of the known methods for the control of fleas gives all round satisfaction, especially since most of the known control methods rely upon the compositions containing the active substance being applied to the habitat of the various flea stages. In view of the complex life cycle of the fleas, however, this application is very laborious, time-consuming and/or unreliable, i. e. not particularly promising in the long term. Only in the short term, it may be possible to achieve a certain alleviation with these known methods. If, for example, the control is targeted at the treatment of the fully grown fleas in the coat, which is usually accomplished by applying an anti-flea composition to the coat of the host animal, the different juvenile stages of the fleas, which live not only in the coat of the animal, but also mainly at all of the places with which the infested animal comes into contact, are totally disregarded. A great number of conventional methods of control are known, which, however, have various disadvantages. If, for example, flea combs, which are surface-coded with an insecticide, are used, the keeper of the animal has to comb the animal intensively and frequently. The use of corresponding anti-flea shampoos is not possible in many cases, since most of the animals infested can be bathed only with difficulty, if at all. Moreover, the effect of such a bath treatment lasts for about a week at most The same problems are to be reckoned with when using oil rubs or rinses. The animals also do not generally submit, without some resistance, to the use of powders. It is virtually unavoidable, that the keeper of the animal also will come into contact with the composition to a greater or lesser extent. When sprays are used, most animals, especially cats, take to flight or react aggressively at the mere noise of the spray. Furthermore, sprays also have the disadvantages mentioned in connection with powders, added to which they are even more finely dispersed in the atmosphere and therefore can be inhaled by the keeper and the animal. Frequently, fleas are also controlled with so-called flea collars, which show a good effect temporarily. One weakness found with this treatment, however, is the locally very limited application. In general, the conventional methods, which aim at killing the adult flea, provide such unsatisfactory results mainly, because they depend upon the patience and the skill of the keeper in dealing with the infested host animal. Another aspect, that has not been given sufficient attention in the case of the conventional methods, is the fact that, because of the particular life cycle of the fleas, the host animals are re-infested over and over again, on the one hand because their contact with the flea eggs, flea larvae and young adult fleas in the environment of the animals is unavoidable and, on the other hand, because many animals come into contact again and again with infested members of their own species. Using the known methods, the continual re-infestation is not adequately prevented, or the prevention is achievable only with high application rates of the parasiticidal compositions.

In numerous regions of the earth, the conditions under which animals, especially domestic animals and pets, are kept, greatly encourage the spread not only of ectoparasites, but also, in particular, of endoparasites. These endoparasites include especially those pests generally referred to as helminths, which may infest, for example, domesticated animals, such as pigs, sheep, cows, calves, goats, horses, dogs, cats or poultry. Helminthiases are a serious economic and hygiene problem in domesticated animals. They lead to anaemia, malnutrition, infirmity, weight loss and/or damage to the walls of the intestinal tract or to other organs, and may, if not treated, result in the death of the animal affected. Among the helminths, especially the group of the roundworms (nematodes) causes an often serious infection of the animals. Representatives of the genera Nematodirus, Cooperia or Oesophagostomum live in the intestines, while those of the genera Haemonchus or Ostertagia live in the stomach, and those of the genus Dictyocaulus can be found in the lungs. Parasites of the families Filariidae or Setariidae affect mainly the heart, the blood vessels and the lymph vessels. Other examples of endoparasites capable of causing great damage, especially in dogs, are the representatives of the genus Dirofilaria, especially *Dirofilaria immitis* (heart worm).

As outlined hereinbefore, a great number of compositions for controlling parasites in and on animals have already been proposed. As also outlined hereinbefore, the properties of these known compositions are not always, however, entirely satisfactory, and, therefore, there is a need to make available further parasiticidally active compositions, especially for the control of insects, representatives of the order Acarina or parasitic worms. This problem is solved according to the invention by the provision of the instant composition.

The present invention accordingly relates to a composition for controlling parasites, in and on animals, which comprises, as active ingredient, a combination, in variable proportions, of at least one parasiticidally active compound, in free form or in salt form, selected from the N-phenyl-N'-benzoyl-urea class of substances, and at least one parasiticidally active compound, in free form or in salt form, selected from the milbemycin, avermectin, milbe-mycin oxime, moxidectin, ivermectin, abamectin and doramectin classes of substances.

The invention relates preferably to a corresponding composition which comprises, as active ingredient, at least one compound of formula

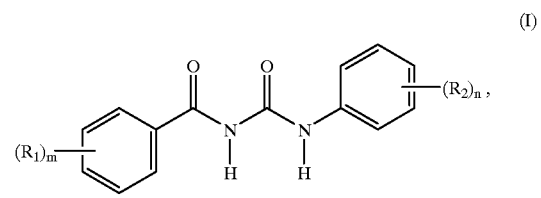

(I)

wherein $R^1$ is halogen, $C_1$–$C_8$alkyl, $C_3$–$C_8$cycloalkyl, halo-$C_3$–$C_8$cycloalkyl, halo-$C_1$–$C_8$alkyl, $C_1$–$C_8$alkoxy, $C_1$–$C_4$alkoxy-$C_1$–$C_4$alkyl or halo-$C_1$–$C_8$alkoxy;

$R_2$ is halogen, $C_1$–$C_8$alkyl, $C_3$–$C_8$cycloalkyl, halo-$C_1$–$C_8$alkyl, halo-$C_3$–$C_8$cycloalkyl, $C_1$–$C_8$alkoxy, $C_3$–$C_8$cycloalkoxy, halo-$C_3$–$C_8$cycloalkoxy, halo-$C_1$–$C_8$alkoxy, aryloxy or heteroaryloxy, substituted aryloxy or heteroaryloxy or a group —$CH_2$—O—N=$C(R_3)R_4$;

$R_3$ and $R_4$ are each, independently of the other, $C_1$–$C_4$alkyl, $C_3$–$C_8$cycloalkyl or aryl, each of which is unsubstituted or substituted;

m is 0 to 5, where, when m is greater than 1, the radicals $R_1$ are the same or different; and n is 0 to 5, where, when n is greater than 1, the radicals $R_2$ are the same or different;

in free form or in salt form, and at least one compound of formula

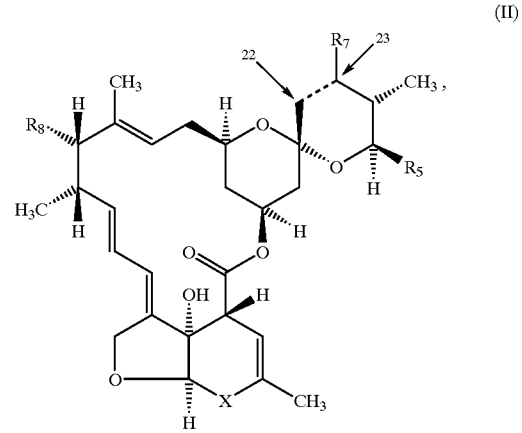

(II)

wherein $R_5$ is $C_1$–$C_4$alkyl or $C_2$–$C_4$alkenyl;

the bond between the atoms 22 and 23 is a single bond or a double bond;

—X— is a group

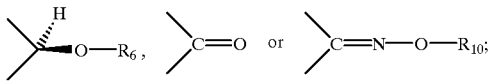

$R_6$ is hydrogen, unsubstituted or substituted $C_1$–$C_8$alkyl, unsubstituted or substituted aryl, —C(=O)$R_{17}$ or —Si($R_{18}$)($R_{19}$)($R_{20}$);

$R_7$ is hydrogen or hydroxy, $R_7$ being hydrogen when the bond between the atoms 22 and 23 is a double bond;

$R_8$ is hydrogen, $C_1$–$C_8$alkyl, $C_2$–$C_8$alkenyl, $C_2$–$C_8$alkynyl, aryl, substituted aryl or a group —OR$_9$ or —SR$_9$;

$R_9$ is $C_1$–$C_8$alkyl, $C_2$–$C_8$alkenyl, $C_2$–$C_8$alkynyl, aryl, C(=O)$R_{16}$, substituted $C_1$–$C_8$alkyl, $C_2$–$C_8$alkenyl, $C_2$–$C_8$alkynyl or aryl, or unsubstituted or substituted heterocyclyl;

$R_{10}$ is hydrogen, unsubstituted or substituted $C_1$–$C_8$alkyl, aryl-$C_1$–$C_4$alkyl, —(CH$_2$)$_o$COR$_{11}$ or —SO$_2$—R$_{15}$;

$R_{11}$ is hydrogen, $C_1$–$C_8$alkyl, aryl-$C_1$–$C_8$alkyl, $C_2$–$C_8$alkenyl, $C_2$–$C_8$alkynyl, $C_1$–$C_8$alkoxy, $C_2$–$C_8$alkenyloxy, $C_2$–$C_8$alkynyloxy, aryl, aryloxy, —N(R$_{12}$)R$_{13}$, —(CH$_2$)$_p$COOR$_{14}$, or $C_1$–$C_8$alkyl or $C_1$–$C_8$alkoxy substituted by $C_1$–$C_4$alkoxy, halogen or by nitro, or aryl, aryloxy or aryl-$C_1$–$C_8$alkyl substituted by $C_1$–$C_4$alkyl, halo-$C_1$–$C_4$alkyl, $C_1$–$C_4$alkoxy, halo-$C_1$–$C_4$alkoxy, halogen or by nitro;

$R_{12}$ and $R_{13}$ are each, independently of the other, hydrogen, $C_1$–$C_8$alkyl, phenyl, or $C_1$–$C_8$alkyl or phenyl substituted by $C_1$–$C_4$alkoxy, halogen or by nitro;

$R_{14}$ is hydrogen or unsubstituted or substituted $C_1$–$C_8$alkyl;

$R_{15}$ is $C_1$–$C_8$alkyl or aryl, each of which is unsubstituted or substituted;

$R_{16}$ is hydrogen, $C_1$–$C_8$alkyl, $C_1$–$C_8$alkoxy or aryl, each of which is unsubstituted or substituted, $R_{17}$ is hydrogen, $C_1$–$C_8$alkyl, $C_1$–$C_8$alkoxy or aryl, each of which is unsubstituted or substituted;

$R_{18}$, $R_{19}$ and $R_{20}$ are each, independently of the others, $C_1$–$C_8$alkyl, $C_1$–$C_8$alkoxy or aryl, each of which is unsubstituted or substituted, o is 0, 1, 2, 3 or 4; and p is 0, 1, 2, 3 or 4;

in free form or in salt form.

A compound I or II, which has at least one basic centre, can form, for example, acid addition salts. These acid addition salts are formed, for example, with strong inorganic acids, such as mineral acids, for example perchloric acid, sulfuric acid, nitric acid, nitrous acid, a phosphoric acid or a hydrohalic acid, with strong organic carboxylic acids, such as unsubstituted or substituted, for example halogen-substituted, $C_1$–$C_4$alkanecarboxylic acids, for example acetic acid, or unsaturated or saturated dicarboxylic acids, for example oxalic acid, malonic acid, succinic acid, maleic acid, fumaric acid or phthalic acid, or hydroxycarboxylic acids, for example ascorbic acid, lactic acid, malic acid, tartaric acid or citric acid, or benzoic acid, or with organic sulfonic acids, such as unsubstituted or substituted, for example halogen-substituted, $C_1$–$C_4$alkane- or arylsulfonic acids, for example methane- or p-toluenesulfonic acid. A compound I or II, which has at least one acidic group, can form salts with bases. Suitable salts with bases are, for example, metal salts such as alkali metal salts or alkaline earth metal salts, for example sodium salts, potassium salts or magnesium salts, or salts with ammonia or with an organic amine, such as morpholine, piperidine, pyrrolidine, a mono-, di- or tri-lower-alkylamine, for example ethyl-, diethyl-, triethyl- or dimethyl-propyl-amine, or a mono-, di- or trihydroxy-lower-alkylamine, for example mono-, di- or triethanolanine. Moreover, corresponding internal salts may also be formed, where possible. Preferred salts within the scope of the invention are veterinarily advantageous salts. Due to the close relationship between a compound I or II in free form and in the form of the salts thereof, a free compound I or II, or the salts thereof, respectively, are to be understood analogously hereinabove and hereinafter as meaning, if appropriate, also the corresponding salts and the free compounds I or II, respectively. Generally preferred is, in each case, the free form. In the case of salts, the veterinarily acceptable salt forms are preferred.

The compounds II, wherein —X— is

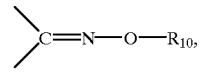

may occur as syn-isomers or anti-isomers in respect of the C=N-double bond. According to the invention, both forms are included, both the pure isomers and mixtures of isomers being meant.

Unless defined otherwise, the general terms used hereinbefore and hereinafter have the meanings given below.

Halogen—as a group per se and as a structural unit of other groups and compounds, such as of haloalkyl, halocycloalkyl, halocycloalkoxy and haloalkoxy,—is fluorine, chlorine, bromine or iodine, especially fluorine, chlorine or bromine, more especially fluorine or chlorine.

Unless defined otherwise, groups and compounds containing carbon atoms each contain preferably from 1 up to and including 20, more preferably from 1 up to and including 18, most preferably from 1 up to and including 10, especially from 1 up to and including 6, most especially from 1 up to and including 4, especially from 1 up to and including 3, carbon atoms.

Alkyl—as a group per se and as a structural unit of other groups and compounds, such as of haloalkyl, alkoxy, alkoxyalkyl, arylalkyl and haloalkoxy,—is either straight-chained, e. g. methyl, ethyl, n-propyl, n-butyl, n-hexyl, n-octyl, n-decyl, n-dodecyl, n-hexadecyl or n-octadecyl, or branched, e. g. isopropyl, isobutyl, sec-butyl, tert-butyl, isopentyl, neopentyl or isohexyl.

Alkenyl—as a group per se and as a structural unit of other groups and compounds, such as of alkenyloxy,—is straight-chained or branched, e. g. vinyl, 2-methylvinyl, allyl, but-1-en-1-yl or isopropenyl, especially allyl, Alkynyl—as a group per se and as a structural unit of other groups and compounds, such as of alkynyloxy,—is straight-chained or branched, e. g. ethynyl, prop-1-yn-1-yl, propargyl or but-1-yn-3-yl, especially propargyl.

Halo-substituted carbon-containing groups and compounds, such as haloalkyl, halocycloalkyl, halocycloalkoxy and haloalkoxy, may be partially halogenated or perhalogenated, and, in the case of multiple halogenation, the halogen substituents may be identical or different. Examples of haloalkyl—as a group per se and as a structural unit of other groups and compounds, such as of haloalkoxy,—are methyl substituted by from one to three fluorine, chlorine and/or bromine atoms, such as $CHF_2$, $CF_3$ or $CH_2Cl$; ethyl substituted by from one to five fluorine, chlorine and/or bromine atoms, such as $CH_2CF_3$, $CF_2CF_3$, $CF_2CCl_3$, $CF_2CHCl_2$, $CF_2CHF_2$, $CF_2CFCl_2$, $CH_2CH_2Cl$, $CF_2CHBr_2$, $CF_2CHClF$, $CF_2CHBrF$ or $CClFCHClF$; propyl or isopropyl substituted by from one to seven fluorine, chlorine and/or bromine atoms, such as $CH_2CHBrCH_2Br$, $CF_2CHFCF_3$, $CH_2CF_2CF_3$, $CF_2CF_2CF_3$, $CH(CF_3)_2$ or $CH_2CH_2CH_2Cl$; and butyl or one of its isomers substituted by from one to nine fluorine, chlorine and/or bromine atoms, such as $CF(CF_3)CHFCF_3$, $CF_2(CF_2)CF_3$ or $CH_2(CF_2)_2CF_3$. Examples of halocycloalkyl—as a group per se and as a structural unit of other groups and compounds, such as of halocycloalkoxy,—are 2,2-difluorocyclopropyl or 2,2-dichlorocyclopropyl.

Cycloalkyl—as a group per se and as a structural unit of other groups and compounds, such as of halocycloalkyl, halocycloalkoxy and cycloalkoxy,—is cyclopropyl, cyclobutyl, cyclopentyl, cyclohexyl, cycloheptyl or cyclooctyl. Cyclopropyl is preferred Aryl—as a group per se and as a structural unit of other groups and compounds, such as of aryloxy,—is preferably phenyl or naphthyl, especially phenyl.

Alkoxyalkyl is preferably alkyl substituted by two or preferably one alkoxy radical, e. g. methoxymethyl or 2-methoxyethyl.

Arylalkyl is preferably alkyl substituted by two or preferably one aryl radical, e. g. benzyl or 2-phenylethyl.

Heteroaryl in heteroaryloxy radicals is preferably an aromatic, monocyclic or bicyclic, ring system, which system comprises one or two rings, selected from the group consisting of 5- and 6membered rings, which system is unsubstituted or substituted by one or two substituents, selected from the group consisting of halogen, nitro, $C_1$–$C_8$alkoxy, halo-$C_1$–$C_8$alkoxy, cyano, hydroxy, $C_1$–$C_8$alkyl and halo-$C_1$–$C_8$alkyl, and which system contains 1 or 2 hetero atoms, selected from the group consisting of nitrogen, oxygen and sulfur atoms. Preferred are ring systems having one or two ring nitrogen atoms, especially pyridyl, pyrimidyl and quinolyl, most especially unsubstituted pyridyl or pyrimidyl, chloro-pyridyl, trifluoromethyl-pyridyl, nitro-pyridyl, chloro-trifluoromethyl-pyridyl and chloroquinolyl.

Heterocyclyl is, for example, heteroaryl, for example as defined hereinbefore, or is preferably a non-aromatic, preferably 5- or 6-membered monocyclic, ring system, which system is unsubstituted or preferably substituted by 1 to 4 substituents, selected from the group consisting of halogen, $C_1$–$C_8$alkyl, halo-$C_1$–$C_8$alkyl, $C_1$–$C_8$alkoxy, halo-$C_1$–$C_8$-alkoxy, hydroxy, nitro, cyano and unsubstituted or mono- to tetra-substituted heterocyclyloxy, the substituents of substituted heterocyclyloxy being selected from the group consisting of $C_1$–$C_8$alkyl, $C_1$–$C_8$alkoxy and hydroxy, and which system contains 1 or 2 hetero atoms, selected from the group consisting of nitrogen, oxygen and sulfur atoms. Preferred are ring systems having a ring oxygen atom, such as oxacyclopentyl or preferably oxacyclohexyl, especially the 4($\alpha$-L-oleandrosyl)-$\alpha$-L-oleandrose group.

A substituted aryl, aryloxy, alkyl, alkoxy, alkenyl or alkynyl group carries, for example, two or preferably one substituent, selected, for example, from the group consisting of halogen, $C_1$–$C_8$alkyl, halo-$C_1$–$C_8$alkyl, $C_1$–$C_8$alkoxy, halo-$C_1$–$C_8$alkoxy, hydroxy, nitro and cyano.

Especially preferred within the scope of the present invention is a corresponding composition, that comprises, as active ingredient, on the one hand at least one compound of the formula I, selected from any one of the following groups (1) to (11):

(1) a compound of formula I, wherein $R_1$, is halogen, especially fluorine, most especially wherein $(R_1)_m$ is 2,6-difluorine;
(2) a compound of formula I, wherein $R_2$ is halogen, halo-$C_1$–$C_4$alkyl, halo-$C_1$–$C_4$alkoxy or substituted pyridyloxy, and n is 1, 2, 3 or 4, especially wherein $R_2$ is fluorine, chlorine, halo-$C_1$–$C_3$alkoxy or chloro-trifluoromethyl-pyridyloxy;
(3) the compound 1-[2,5-dichloro4(1,1,2,3,3,3-hexafluoroprop-1-oxy)-phenyl]-3-(2,6difluorobenzoyl)-urea (Lufenuron);
(4) the compound 1-[3-(3-chloro-5-trifluoromethyl-pyrid-2-yloxy)-4-chloro-phenyl]-3-(2,6difluorobenzoyl)-urea (Fluazuron);
(5) the compound 1-(4-chlorophenyl)-3-(2,6difluorobenzoyl)-urea (Diflubenzuron);
(6) the compound 1-[3,5-dichloro-4-(1,1,2,2-tetrafluoroethoxy)-phenyl]-3-(2,6difluorobenzoyl)-urea (Hexaflumuron);
(7) the compound 1-(3,5-dichloro-2,4-difluoro-phenyl)-3-(2,6difluorobenzoyl)-urea (Teflubenzuron);
(8) the compound 1-[3,5-dichloro4(3-chloro-5-trifluoromethyl-pyrid-2-yloxy)-phenyl]-3-(2,6difluorobenzoyl)-urea (Chlorfluazuron);
(9) the compound 1-(2-chlorobenzoyl)-3-(4trifluoromethoxyphenyl)-urea (Triflumuron);
(10) the compound 1-[4(2-chloro-4-fuoromethyl-phenoxy)-2-fluoro-phenyl]-3-(2,6difluorobenzoyl)-urea (Flufenoxuron);
(11) the compound 1-[$\alpha$-(4-chloro-$\alpha$-cyclopropyl-benzylideneaminooxy)p-tolyl]-3-(2,6-difluorobenzoyl)-urea (Flucycloxuron);
and on the other hand at least one compound of the formula II, selected from any one of the following groups (12) to (21):
(12) a compound of formula II, wherein $R_5$ is methyl, ethyl, isopropyl or sec-butyl, especially methyl or ethyl;
(13) a compound of formula II, wherein —X— is

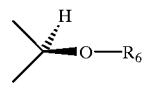

and $R_6$ is hydrogen or methyl, especially hydrogen;
(14) a compound of formula II, wherein —X— is

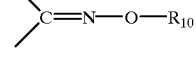

and $R_{10}$ is hydrogen or methyl, especially hydrogen;
(15) a compound of formula II, wherein $R_8$ is hydrogen or the 4($\alpha$-L-oleandrosyl)-$\alpha$-L-oleandrose group, especially hydrogen;
(16) a compound of formula II, wherein the bond between the atoms 22 and 23 is a single bond and $R_7$ is hydrogen;
(17) a compound of formula II, wherein $R_5$ is methyl, ethyl or isopropyl, especially methyl or ethyl, —X— is

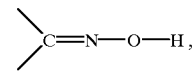

$R_7$ and $R_8$ are hydrogen and the bond between the atoms 22 and 23 is a single bond;

(18) a mixture of two compounds of formula II, wherein —X— is

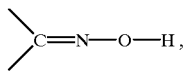

R$_7$ and R$_8$ are hydrogen, the bond between the atoms 22 and 23 is a single bond and in approximately 20% by weight of the mixture R$_5$ is methyl and in approximately 80% by weight of the mixture R$_5$ is ethyl;

(19) a compound of formula II, wherein —X— is

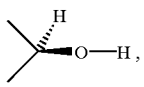

R$_7$ and R$_8$ are hydrogen, the bond between the atoms 22 and 23 is a single bond and R$_5$ is methyl (milbemycin A$_3$), or R$_5$ is ethyl (milbemycin A$_4$), or R$_5$ is isopropyl (milbemycin D);

(20) a compound of formula II, wherein —X— is

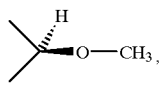

R$_8$ is the 4(α-L-oleandrosyl)-α-L-oleandrose group, and a) the bond between the atoms 22 and 23 is a single bond, R$_7$ is OH and R$_5$ is isopropyl (avermectin A$_{2b}$), or R$_5$ is sec-butyl (avermectin A$_{2a}$; or b) the bond between the atoms 22 and 23 is a double bond, R$_7$ is H and R$_5$ is isopropyl (avermectin A$_{1b}$), or R$_5$ is sec-butyl (avermectin A$_{1a}$);

(21) a compound of formula II, wherein —X— is

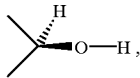

R$_8$ is the 4(α-L-oleandrosyl)-α-L-oleandrose group, and a) the bond between the atoms 22 and 23 is a single bond, R$_7$ is OH and R$_5$ is isopropyl (avermectin B$_{2b}$), or R$_5$ is sec-butyl (avermectin B$_{2a}$); or b) the bond between the atoms 22 and 23 is a double bond, R$_7$ is H and R$_5$ is isopropyl (avermectin B$_{1b}$), or R$_5$ is sec-butyl (avermectin B$_{1a}$).

Very especially preferred within the scope of the present invention is a corresponding composition, that comprises, as active ingredient, either

(22) Lufenuron and a mixture of two compounds of formula II, wherein —X— is

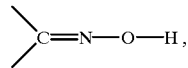

R$_7$ and R$_8$ are hydrogen, the bond between the atoms 22 and 23 is a single bond and R$_5$ is on the one hand methyl and on the other hand ethyl; or

(23) Fluazuron and a mixture of two compounds of formula II, wherein —X— is

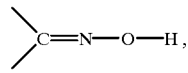

R$_7$ and R$_8$ are hydrogen, the bond between the atoms 22 and 23 is a single bond and R$_5$ is on the one hand methyl and on the other hand ethyl; or

(24) Lufenuron and milbemycin oxime.

The compounds of formulae I and II are known or can be prepared in accordance with methods that are known per se. Specifically:

Lufenuron is known from EP-B1-0 179 022;

Fluazuron is known from EP-A-0 079 311;

Diflubenzuron is known from The Pesticide Manual, 9th Ed (1991), The British Crop Protection Council, London, page 281;

Teflubenzuron is known from The Pesticide Manual, 9th Ed (1991), The British Crop Protection Council, London, page 790;

Chlorfluazuron is known from The Pesticide Manual, 9th Ed (1991), The British Crop Protection Council, London, page 143;

Hexaflumuron is known from The Pesticide Manual, 9th Ed. (1991), The British Crop Protection Council, London, page 471;

Triflumuron is known from The Pesticide Manual, 10th Ed. (1994), The British Crop Protection Council, London, page 1023;

Flufenoxuron is known from The Pesticide Manual, 10th Ed. (1994), The British Crop Protection Council, London, page 483;

Flucycloxuron is known from The Pesticide Manual, 10th Ed. (1994), The British Crop Protection Council, London, page 478;

the compounds of formula II, wherein —X— is

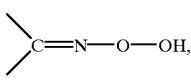

R$_7$ and R$_8$ are hydrogen, the bond between the atoms 22 and 23 is a single bond and R$_5$ is methyl or ethyl, are known under the terms milbemycin oxime A$_3$ (methyl derivative) and milbemycin oxime A$_4$ (ethyl derivative), respectively, and are described in EP-B1-0 110 667;

milbemycin A$_3$ and milbemycin A$_4$ are known from U.S. Pat. No. 3,950,360;

milbemycin D is known from U.S. Pat. No. 4,346,171; and avermectin $A_{1a}$, avermectin $A_{1b}$, avermectin $A_{2a}$, avermectin $A_{2b}$, avermectin $B_{1a}$, avermectin $B_{1b}$, avermectin $B_{2a}$ and avermectin $B_2b$ are described in DE-OS 27 17 040.

Surprisingly, the composition according to the invention is outstandingly suitable for controlling curatively and, surprisingly, also preventively a very advantageous spectrum of parasites in and on animals, even at low rates of application, while being well tolerated by, for example, warm-blooded animals, fish and plants. The composition according to the invention is effective against all or individual development stages of normally sensitive and also resistant animal parasites, such as insects, representatives of the order Acarina or parasitic worms, such as helminths. The good pesticidal activity of the composition according to the invention may manifest itself directly, that is to say in the death of the parasites, which occurs immediately or only at a later date, or indirectly, for example in a reduced oviposition and/or a reduced hatching rate of corresponding parasites, the good activity corresponding, for example, to a mortality and/or a reduction in the oviposition and/or in the hatching rate of at least 50 to 60%.

The parasites, which can be controlled with the composition according to the invention, include, for example:

of the order Acarina e. g. representatives of the families Argasidae, Dermanyssidae, Ixodidae, Psoroptidae or Sarcoptidae and representatives of the species Amblyomma spp., Anocentor spp., Argas spp., Boophilus spp., Cheyletiella spp., Chorioptes spp., Demodex spp., Dermacentor spp., Dermanyssus spp., Haemophysalis spp., Hyalomma spp., Ixodes spp., Lynxacarus spp., Notoedres spp., Ornithodoros spp., Ornithonyssus spp., Otobius spp., Otodectes spp., Pneumonyssus spp., Psoroptes spp., Rhipicephalus spp. or Sarcoptes spp.;

of the order Anoplura e. g. representatives of the species Haematopinus spp., Linognathus spp., Pediculus spp., Pemphigus spp. or Phylloxera spp.;

of the order Diptera e. g. representatives of the species Aedes spp., Anopheles spp., Calliphora spp., Chrysomyia spp., Chrysops spp., Cochliomyia spp., Culex spp., Culicoides spp., Cuterebra spp., Dermatobia spp., Gastrophilus spp., Glossina spp., Haematobia spp., Haematopota spp., Hippobosca spp., Hypoderma spp., Lucilia spp., Lyperosia spp., Melophagus spp., Oestrus spp., Phlebotomus spp., Phormia spp., Sarcophaga spp., Simulium spp., Stomoxys spp., Tabanus spp., Tannia spp. or Tipula spp.;

of the order Mallophaga e. g. representatives of the species Damalina spp., Felicola spp., Heterodoxus spp. or Trichodectes spp.;

of the class Nematoda e. g. representatives of the families Filariidae or Setariidae, representatives of the genera Ascaris, Bunostomum, Chabertia, Cooperia, Haemonchus, Nematodirus, Oesophagostomum, Ostertagia, Trichostrongylus or Trichuris and representatives of the species Ancylostoma spp., Ascaridia spp., Capillaria spp., Dictyocaulus spp., Dirofilaria spp., Heterakis spp., Oxyuris spp., Parascaris spp., Strongyloides spp., Strongylus spp., Toxascaris spp., Toxocara spp., Trichonema spp., Trichuris spp. or Uncinaria spp.;

of the order Siphonaptera e. g. representatives of the species Ceratophyllus spp., Ctenocephalides spp. or Xenopsylla spp.; and of the class Trematoda e. g. representatives of the family Fasciolidae and representatives of the species Fasciola spp..

These parasites infest numerous, especially warm-blooded, for example domesticated, animals, such as calves, cats, cattle, cows, dogs, goats, horses, pigs, poultry or sheep, which can be treated with the composition according to the invention.

Especially, by means of the composition according to the invention, *Ctenocephalides canis* and/or *C. felis* are controlled simultaneously with *Ancylostoma caninum, Dirofilaria immitis, Toxocara canis* and/or *Trichuris vulpis*; very especially, by means of the composition according to the invention, *C. felis* and *D. immitis* are controlled simultaneously on and in dogs.

In particular, it has surprisingly been found, that the parasiticidal activity of the composition according to the invention, if compared with the combined parasiticidal activities of the individual compounds I and II together forming the active ingredient of the instant composition, is not only additive, as can be expected in principle, but also shows a surprising synergistic effect. In this connection, the term "synergistic effect" is neither limited to the pure parasiticidal activity against a certain parasite species, nor is it necessary, that this term relates at all to the pure parasiticidal activity, but this term can relate to any property of the instant composition, which is advantageous, if compared with the combined corresponding properties of the individual compounds I and II together forming the active ingredient of the instant composition. As examples of such advantageous properties of the instant composition there may be mentioned: a broadening in the spectrum of the parasiticidal activity towards additional or different parasites, for example towards a resistant parasite species; a reduction in the rates of application of the compounds I and/or II; a sufficient degree of parasite control by means of the instant composition even in cases where the individual compounds I and II together forming the active ingredient of the instant composition are totally ineffective due to their extremely low rates of application; an advantageous behaviour in the case of being formulated and/or applied, for example if being ground, sieved, compressed, emulsified, dissolved, dispersed or sprayed; an improved storage stability; a better light stability; a better heat stability; an advantageous behaviour in the case of being degraded; a better toxicology profile; an improved ecotoxicology behaviour, other advantages familiar to those skilled in the art.

Surprisingly, with the aid of specific methods of administration to the animals, for example by external treatment with, but especially by systemic administration of, a composition according to the invention, it is possible to eliminate the above-mentioned ectoparasites very quickly and completely and thereby intervene obstructively in the complex life cycle of these parasites, and at the same time achieve effective control of the above-mentioned endoparasites. Since the composition according to the invention still displays its excellent parasiticidal effect fully when administered to the host animal systemically, i. e. orally, parenterally or by implant, it is possible by controlled periodic administration of the composition to interrupt the described continually recurring re-infestation of the host animal by the various parasites in a simple manner, until all of the young parasite stages in the area where the host animal lives are controlled. The parasites are killed and prevented from reproducing, and the juvenile stages are prevented from reaching adulthood and can no longer infest the host animal, as a result of which the area where the host animal lives can be kept free of parasites permanently.

The present invention further relates, therefore, to a method of controlling parasites in and on animals, for example domestic animals and productive livestock, which comprises administering to the host animals a composition according to the invention, in a parasiticidally effective amount, preferably systemically, i. e. orally, parenterally or by implant. A special form of this method comprises administering the different active ingredient compounds I and II that are to be used to the host animal, in a parasiticidally effective amount, not simultaneously but within a short interval, that is to say within one week at most, especially on the same day. In that method, it makes no difference whether the modes of administration are identical, that is to say whether the active ingredient compounds are all administered for example orally, or are different, that is to say whether one or more of the active ingredient compounds is/are administered for example orally and others are administered, after a short interval, for example parenterally.

What is very remarkable with regard to the present invention is that the full effect is still achieved even when the composition according to the invention is administered to the host animal in relatively low concentrations. With the endo- and ecto-parasites being killed completely and simultaneously after the systemic administration of the composition, it is now possible to achieve simultaneous elimination of the parasites. By combining this systemic use of the composition with secondary measures, such as disinfection of the abode of the host animal, it is possible to dispose of the parasite problem even more quickly; even without those secondary measures, however, the parasite population will be reduced completely or at least to an acceptable minimum within a few weeks or, at most, months. The complex life cycles of, for example, fleas and ticks are interrupted, therefore, and the continual re-infestation of the host animals in their preferred living area by the eggs that are scattered everywhere and by the larvae that emerge therefrom is prevented. The way in which the parasites are controlled is that, although eggs are laid by the adults that are fully replete with blood, which, in the case of ticks, drop off the host animal but, in the case of fleas, remain on the host animal, no larvae or only a few larvae are able to develop from those eggs. While those few larvae can in turn infest the host animal, they are unable to develop further, whereby the cycle is broken. The composition according to the invention therefore has especially a preventive effect against the various types of parasites, but also has a curative effect inasmuch as, for example, tick larvae that are on the host animal but have not yet ingested any active substance via the described cycle are also prevented from developing further into adults upon treatment of the host with a topical pour-on or spot-on formulation. An important advantage of the method according to the invention resides in the fact that the life cycle of carriers is also interrupted. These carriers are, for example, various species of mosquitoes that are responsible for transmitting endoparasites, such as Filariae.

It is essential that the composition according to the invention is so administered that the compounds I and II can be ingested by endoparasites, ectoparasites and also by other pests, that come into consideration as vectors for the transmission of endoparasites, with the blood of the host animal in an amount sufficient that the eggs laid by the adults and also the larvae no longer develop. This is achieved with the composition according to the invention using various forms of administration, for example by administering the formulated composition orally. "Formulated" means in this case, for example, in the form of a powder, a tablet, a granule, a capsule, a dragée, an emulsion, a foam, in microencapsulated form, etc., the formulation not necessarily having to be given to the animal directly but advantageously being mixed with its food. All compositions that are to be administered orally may, of course, contain, in addition to customary formulation auxiliaries, also other additives that encourage the voluntary intake of the composition by the host animal, for example suitable flavourings. Owing to its easy practicability, the oral administration is one of the preferred objects of this invention. Other modes of administration are the parenteral administration, for example the subcutaneous or the intravenous injection, and, as a long-term formulation (depot form), the application in the form of an implant or in the form of an injection of microcapsules (so-called "microspheres").

Oral administration also includes, for example, the serving of animal food, for example dog or cat food, that already contains the active ingredient mixed with it, for example in the form of biscuits, lozenges, water-soluble capsules or tablets, in water-soluble form which can be added in drops to the food, or in other forms that can be admixed with the animal food. The administration of veterinary medicine additives to animal food is best known in the animal health sector. Usually, a so-called premix is prepared first, in which the active substances are dispersed in a liquid or finely distributed in solid carriers. That premix may normally comprise, depending upon the desired final concentration in the food, approximately from 0.1 to 800 g of the active substances per kg of premix. In addition, it is known that active substances may be hydrolysed or made weaker by the ingredients of the food. Such active substances are routinely formulated in a protective matrix, e. g. in gelatin, before being added to the premix.

Parenteral administration includes, for example, subcutaneous, dermal, intramuscular and even intravenous administration of injectable formulations. Apart from conventional syringes with needles, needleless pressure gun devices and also pour-on and spot-on formulations may be useful for this purpose.

By choosing a suitable formulation it is possible to enhance the penetration capacity of the active ingredient through the living tissue of the animal and maintain its availability. This is important when, for example, one or more sparingly soluble active substances are used, the low solubility of which necessitates a measure that promotes the solubility since the body fluid of the animal is capable of dissolving only small amounts of the active substances all at once.

The active substances may also be present in a matrix formulation which, by physical means, prevents their decomposition and maintains their constant availability. This matrix formulation is injected into the body and remains there as a kind of depot from which the active substances are continuously released. Such matrix formulations are known to those skilled in the art. They are generally wax-like, semi-solid excipients, for example vegetable waxes, polyethylene glycols having a high molecular weight, or copolymers of degradable polyesters.

A high availability of the active ingredient is also obtained by inserting an implant of the active substances into the animal. Implants include all devices that can be inserted into the body of the animal to release the substances. Such implants are widely used in veterinary medicine and often consist of silicone-containing rubber. The active substances are dispersed in the solid rubber or located inside a hollow rubber body. Care should be taken to select active substances that are soluble in the rubber implant since they are first dissolved in the rubber and then seep continuously from the rubber material into the body fluid of the animal to be treated. The release rate of the active substances from the implant, and hence the period for which the implant is effective, are generally determined by the accuracy of the calibration (amount of active ingredient in the implant) of the implant, the environment of the implant and the polymer formulation from which the implant is made. The administration of the active ingredient by means of an implant is another preferred component of the present invention. Administration in that manner is extremely economical and effective, since a correctly dimensioned implant ensures a constant concentration of the active substances in the tissue of the host animal. Implants can nowadays be fashioned and easily implanted in such a manner that they are capable of delivering the active ingredients over a number of months.

The compounds I and II are each advantageously administered to the animal in a dose of from approximately 0.01 to 800, preferably from approximately 0.1 to 200, especially from approximately 0.5 to 30, mg/kg of body weight. The dose may vary for the same active ingredient from one genus of animal to another and also within one animal genus since it depends inter alia upon the weight and the constitution of the animal. A suitable dose to be administered regularly to the host animal is, for example, in the case of a cat, a dose of 30 mg/kg of body weight of a compound I and 2 mg/kg of body weight of a compound II and, in the case of a dog, a dose of 10 mg/kg of body weight of a compound I and 0.5 mg/kg of body weight of a compound II. The administration is advantageously carried out weekly or especially monthly.

The combination of active substances according to the invention comprises at least one compound I and at least one compound II, preferably in a ratio [compound(s) I: compound(s) II] of from 1:60 to 60:1, especially of from 1:20 to 20:1, more especially from 10:1 to 1:10, most especially from 5:1 to 1:5, and most preferably from 2:1 to 1:2. Especially preferred ratios [compound(s) I: compound (s) II] are 20:1, or 15:1, or 5:1, or 4:1, or 3:1, or 2:1, or 1:1, or 1:2, or 1:3, or 1:4, or 1:5, or 5:2, or 3:2, or 4:3, or 3:4, or 2:3, or 5:3, or 3:5, or 5:4, or 4:5.

The composition according to the invention normally comprises from 0.1 to 99% by weight, preferably from 0.1 to 95% by weight, of the compounds I and II and from 99.9 to 1% by weight, preferably from 99.9 to 5% by weight, of a solid or liquid auxiliary.

As formulation auxiliaries there may preferably be used the materials known from the veterinary medicine for oral or parenteral administration or implants. A number of examples are mentioned hereinafter. Suitable carriers are especially fillers, such as sugars, for example lactose, saccharose, mannitol or sorbitol, cellulose preparations or calcium phosphates, for example tricalcium phosphate or calcium hydrogen phosphate, and also binders, such as starch pastes using, for example, corn, wheat, rice or potato starch, gelatin, tragacanth, methylcellulose, or, if desired, disintegrators, such as the above-mentioned starches, also carboxymethyl starch, crosslinked polyvinylpyrrolidone, agar or alginic acid or a salt thereof, such as sodium alginate. Excipients are especially flow conditioners and lubricants, for example silicic acid, talc, stearic acid or salts thereof, such as magnesium or calcium stearate, or polyethylene glycol. Dragée cores may be provided with suitable, optionally enteric, coatings, there being used, inter alia, concentrated sugar solutions which may comprise gum arabic, talc, polyvinylpyrrolidone, polyethylene glycol or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes, flavourings or pigments may be added to the tablets or dragée coatings, for example for identification purposes or to indicate different doses of the active ingredient Other orally administrable compositions are dry-filled capsules made of gelatin and also soft, sealed capsules made of gelatin and a plasticiser, such as glycerol or sorbitol. The dry-filled capsules may comprise the active ingredient in the form of granules, for example in admixture with fillers, such as lactose, binders, such as starches, or glidants, such as talc or magnesium stearate, and, if desired, stabilisers. In soft capsules, the active ingredient is preferably dissolved or suspended in suitable liquids, such as fatty oils, paraffin oil or liquid polyethylene glycols, to which stabilisers may also be added. Preferred inter alia are capsules that can be both easily bitten and swallowed unchewed Suitable for parenteral administration are especially aqueous solutions of the active ingredient in water-soluble form, e. g. in the form of water-soluble salts, or also suspensions of the active ingredient, such as corresponding oily injection suspensions, there being used suitable lipophilic solvents or vehicles, such as fatty oils, e. g. sesame oil, or synthetic fatty acid esters, e. g. ethyl oleate, or triglycerides, or aqueous injection suspensions that comprise viscosity-increasing substances, e. g. sodium carboxymethylcellulose, sorbitol or dextran, and, if desired, also stabilisers. The formulations may also comprise further auxiliaries, such as binders, antifoams, viscosity regulators, stabilisers and also tackifiers.

The composition according to the invention may be prepared in a manner known per se, for example by means of conventional mixing, granulating, confectioning, dissolving or lyophilising processes. For example, a veterinary composition for oral administration can be obtained by combining the active ingredient with solid carriers, if desired granulating the resulting mixture, and processing the mixture or granules, if desired or necessary after the addition of appropriate excipients, to form tablets or dragée cores.

The following Examples illustrate the invention described above but do not limit the scope thereof in any way. Temperatures are given in degrees Celsius.

FORMULATION EXAMPLES

In the following Formulation Examples, "active ingredient I" denotes one or more compounds I and "active ingredient II" denotes one or more compounds II, in each case in free form or in veterinarily acceptable salt form.

Example 1

Tablets

| Composition (for 1000 tablets): | |
|---|---|
| active ingredient I | 25 g |
| active ingredient II | 1.25 g |
| lactose | 100.7 g |
| wheat starch | 6.25 g |
| polyethylene glycol 6000 | 5.0 g |
| talc | 5.0 g |
| magnesium stearate | 1.8 g |
| demineralised water | q. s. |

Preparation: All of the solid ingredients are first forced through a sieve of 0.6 mm mesh size. Then the active ingredients, the lactose, the talc and half of the starch are mixed. The other half of the starch is suspended in 40 ml of water, and the suspension is added to a boiling solution of the polyethylene glycol in 100 ml of water. The resulting starch paste is added to the main ingredients, and the mixture is granulated, if necessary with the addition of water. The granules are dried overnight at 35°, forced through a sieve of 1.2 mm mesh size, mixed with the magnesium stearate and compressed to form biconcave tablets of approximately 6 mm mesh size.

Example 2
Tablets

| Composition (for 10000 tablets): | |
|---|---|
| active ingredient I | 180.0 g |
| active ingredient II | 3.0 g |
| lactose | 280.8 g |
| potato starch | 274.7 g |
| stearic acid | 10.0 g |
| talc | 217.0 g |
| magnesium stearate | 2.50 g |
| colloidal silica | 32.0 g |
| ethanol | q. s. |

A mixture of the active ingredients, the lactose and 200 g of potato starch is moistened with an ethanolic solution of the stearic acid and granulated through a sieve. After the drying of the granules, the remainder of the potato starch, the talc, the magnesium stearate and the colloidal silica are added thereto, and the mixture is compressed to form tablets, each weighing 0.1 g, which may, if desired, be provided with breaking notches for the finer adjustment of the dose.

Example 3
Capsules

| Composition (for 1000 capsules): | |
|---|---|
| active ingredient I | 20.0 g |
| active ingredient II | 2.0 g |
| lactose | 249.8 g |
| gelatin | 2.0 g |
| corn starch | 10.0 g |
| talc | 15.0 g |
| water | q. s. |

The active ingredients are mixed with the lactose, and the mixture is uniformly moistened with an aqueous solution of the gelatin and granulated through a sieve having a mesh size of 1.2–1.5 mm. The granules are mixed with the dried corn starch and the talc, and portions of 300 mg are introduced into hard gelatin capsules (size 1).

Example 4
Premix (food additive)

0.15 parts by weight of active ingredient I, 0.01 parts by weight of active ingredient II and 4.84 parts by weight of secondary calcium phosphate, argillaceous earth, Aerosil, carbonate or chalk are mixed with 95 parts by weight of an animal food until homogeneous.

Example 5
Premix (food additive)

0.40 parts by weight of active ingredient I, 0.01 parts by weight of active ingredient II and 5.00 parts by weight of Aerosil/chalk (1:1) are mixed with 94.59 parts by weight of a commercial dry food until homogeneous.

Example 6
Emulsifiable concentrate 20 parts by weight of active ingredient I and 1 part by weight of active ingredient II are mixed with 20 parts by weight of the emulsifier (mixture of alkylaryl polyglycol ether with alkylaryl polysulfonates) and 59 parts by weight of a suitable solvent until the solution has been completely homogenised. Emulsions of the desired concentration can be obtained by dilution with water.

Example 7
Soluble powder 25 parts by weight of active ingredient I, 0.5 parts by weight of active ingredient II, 2.5 parts by weight of sodium lauryl sulfate, 3 parts by weight of colloidal silica gel and 69 parts by weight of urea are mixed and ground together until homogeneous.

Other biologically active substances, or additives that have a neutral behaviour towards the active ingredients and do not have any harmful effect on the host animal to be treated, or also mineral salts or vitamins may be added to the described compositions.

Biological Examples (unless defined otherwise, %= percent by weight)

Example 8
Simultaneous action against *Ancylostoma caninum* and *Ctenocephalides felis*

As test animals, 3 dogs (1 female, 2 males) of from 7 to 10.5 kg of body weight and from 2 to 3 years of age are used. As comparison animals, 3 dogs (1 female, 2 males) of from 7.5 to 10 kg of body weight and from 2 to 4 years of age are used. All of the animals are naturally infected with *Ancylostoma caninum*. Immediately after administration of a gelatin capsule comprising 10 mg/kg of body weight of Lufenuron and 0.5 mg/kg of body weight of *Milbemycin oxime*, each of the test animals is infested in the neck region with 20 fleas of the species *Ctenocephalides felis* (16 female and 4 male fleas). The comparison animals are not given any active substances, but are infected in the same manner and at the same time with *Ctenocephalides felis*. During the test period, the flea eggs are collected daily and incubated to determine their viability. A first evaluation of the endoparasites is carried out by comparing the number of worms excreted by the test animals and by the control animals. Already a few days after the treatment, the hatching of flea eggs and the development of adult fleas are completely suppressed. An autopsy reveals that the test animals are completely free of worms. In the untreated animals, neither a significant reduction in the ability of the flea eggs to develop nor a reduction in the number of worms in the gastrointestinal tract are found.

Example 9
Simultaneous action against *Ctenocephalides felis* and *Dirofilaria immitis*

As test animals, 3 dogs (1 female, 2 males) of from 7.5 to 10.2 kg of body weight and from 2 to 4 years of age are used. As comparison animals, 3 dogs (1 female, 2 males) of from 7.0 to 10.1 kg of body weight and from 2 to 4 years of age are used. The test animals are infected subcutaneously with 40 infectious larvae (3rd larval stage) of *Dirofilaria immitis* obtained from infected mosquitoes (*Aedes aegypti*). 30 days later, the test animals are given a gelatin capsule comprising 10 mg/kg of body weight of Lufenuron and 0.5 mg/kg of body weight of *Milbemycin oxime*, and immediately thereafter each of the test animals is infested in the neck region with 20 fleas of the species *Ctenocephalides felis* (16 female and 4 male fleas). The comparison animals are not given any active substances, but are infected in the same manner and at the same time with *Dirofilaria immitis* and *Ctenocepha-*

*lides felis*. Already a few days after the treatment, the hatching of flea eggs and the development of adult fleas are completely suppressed in the test animals. Upon autopsy 200 days after the infection, adult heart worms are no longer found in the lungs and the heart of the treated animals. In the untreated control group, on average 20 *Dirofilaria immitis* adults are found per test animal.

What is claimed is:

1. A method for controlling parasites in or on host animals comprising administering orally to the host animal a parasiticidally effective amount of the composition of a combination of at least one compound of the formula (I)

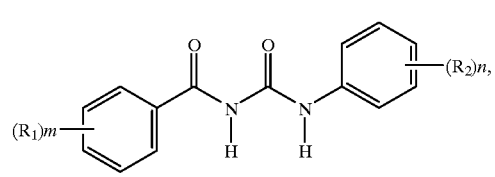

(I)

wherein $R_1$ is halogen, $C_1$-$C_8$alkyl, $C_3$-$C_8$cycloalkyl, halo-$C_3$-$C_8$cycloalkyl, halo-$C_1$-$C_8$alkyl, $C_1$-$C_8$alkoxy, $C_1$-$C_4$alkoxy-$C_1$-$C_4$alkyl or halo-$C_1$-$C_8$alkoxy, $R_2$ is halogen, $C_1$-$C_8$alkyl, $C_3$-$C_8$cycloalkyl, halo-$C_1$-$C_8$alkyl, halo-$C_3$-$C_8$cycloalkyl, $C_1$-$C_8$alkoxy, $C_3$-$C_8$cycloalkoxy, halo-$C_1$-$C_8$alkoxy, halo-$C_3$-$C_8$cycloalkoxy, aryloxy or heteroaryloxy, substituted aryloxy or heteroaryloxy or a group —$CH_2$—O—N=$C(R_3)R_4$, wherein $R_3$ and $R_4$ are each, independently of the other, $C_1$-$C_4$alkyl, $C_3$-$C_8$cycloalkyl or aryl, each of which is unsubstituted or substituted;

m is 0 to 5, and, when m is greater than 1, the radicals $R_1$ are the same or different; and n is 0 to 5, where, when n is greater than 1, the radicals $R_2$ are the same or different;

in free form or in salt form, and at least one compound of the formula (II)

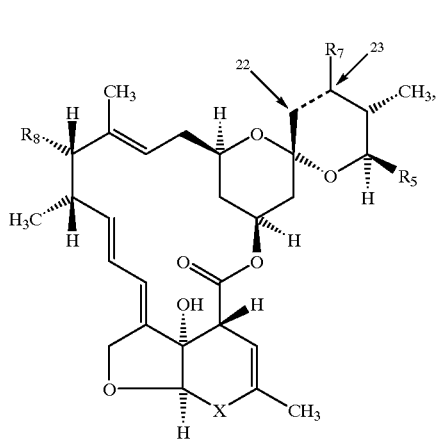

(II)

wherein $R_5$ is $C_1$-$C_4$alkyl or $C_2$-$C_4$alkenyl, the bond between atoms 22 and 23 is a single bond or a double bond X is a group

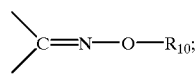

$R_7$ is hydrogen or hydroxy, $R_7$ being hydrogen when the bond between atoms 22 and 23 is a double bond;

$R_8$ is hydrogen, $C_1$-$C_8$alkyl, $C_2$-$C_8$alkenyl, aryl, substituted aryl or a group —$OR_8$ or —$SR_9$, $R_9$ is $C_1$-$C_8$alkenyl, $C_2$-$C_8$alkenyl, $C_2$-$C_8$alkynyl, aryl, $C(=O)R_{16}$, substituted $C_1$-$C_8$alkyl, $C_2$-$C_8$alkenyl, $C_2$-$C_8$alkynyl or aryl, or an unsubstituted or substituted heterocyclic radical;

$R_{10}$ is hydrogen, unsubstituted or substituted $C_1$-$C_8$alkyl, aryl-$C_1$-$C_4$alkyl, —$(CH_2)_oCOR_{11}$ or —$SO_2$—$R_{15}$;

$R_{11}$ is hydrogen, $C_1$-$C_8$alkyl, aryl-$C_1$-$C_8$alkyl, $C_2$-$C_8$alkenyl, $C_2$-$C_8$alkynyl, $C_1$-$C_8$alkoxy, $C_2$-$C_8$alkenyloxy, $C_2$-$C_8$alkynyloxy, aryl, aryloxy, —$N(R_{12})R_{13}$, —$(CH_2)_pCOOR_{14}$, or $C_1$-$C_8$alkyl or $C_1$-$C_8$alkoxy substituted by $C_1$-$C_4$alkoxy, halogen or by nitro, or aryl, aryloxy or aryl-$C_1$-$C_8$alkyl substituted by $C_1$-$C_4$alkyl, halo-$C_1$-$C_4$alkyl, $C_1$-$C_4$alkoxy, halo-$C_1$-$C_4$alkoxy, halogen or by nitro;

$R_{12}$ and $R_{13}$ are each, independently of the other, hydrogen, $C_1$-$C_8$alkyl, phenyl, or $C_1$-$C_8$alkyl or phenyl substituted by $C_1$-$C_4$alkoxy, halogen or by nitro;

$R_{14}$ is hydrogen or unsubstituted or substituted $C_1$-$C_8$alkyl;

$R_{15}$ is $C_1$-$C_8$alkyl or aryl, each of which is unsubstituted or substituted;

$R_{16}$ is hydrogen, $C_1$-$C_8$alkyl, $C_1$-$C_8$alkoxy or aryl, each of which is unsubstituted or substituted;

o is 0, 1, 2, 3 or 4; and p is 0, 1, 2, 3 or 4;

in free form or in salt form;

and a suitable carrier.

2. The method according to claim 1, which comprises the compounds of formulae I and II in free form.

3. The method according to claim 2, which comprises 1-[2,5-dichloro-4-(1,1,2,3,3,3-hexafluoroprop-1-oxy)phenyl-3-(2,6-difluorobenzoyl)urea.

4. The method according to claim 2, which comprises 1-[3-(3-chloro-5-trifluoromethyl-pyrid-2-yloxy)-4-chlorophenyl]-3-(2,6-difluorobenzoyl)urea.

5. The method according to claim 3, which further comprises milbemycin oxime.

6. The method according to claim 4, which comprises milbemycin oxime.

7. A method of controlling parasites in animals wherein a parasiticidally effective amount of a composition according to claim 1 is added to the animal's food.

8. The method according to claim 1 wherein the host animal is a cat or a dog.

9. The method according to claim 1 wherein the parasites comprise insects, acarina or parasitic worms.

10. The method according to claim 1 wherein the parasites comprise ectoparasites of the species *Ctenocephalides felis* or *C. canis* or endoparasites of the species *Ancylostoma caninum, Dirofilaria immitis, Toxocara canis* or *Trichuris vulpis* or both of those ectoparasites and endoparasites.

11. The method according to claim 1 wherein the parasites comprise ectoparasites of the species *Ctenocephalides felis* and endoparasites of the species *Dirofilaria immitis* or both of those ectoparasites and endoparasites.

* * * * *